United States Patent
Arora et al.

(10) Patent No.: US 12,374,465 B2
(45) Date of Patent: Jul. 29, 2025

(54) SYSTEM AND METHOD FOR DETECTION OF A HEART FAILURE RISK

(71) Applicant: Qure.ai Technologies Private Limited, Maharashtra (IN)

(72) Inventors: Charu Arora, Maharashtra (IN); Preetham Putha, Maharashtra (IN); Manoj Tadepalli, Maharashtra (IN)

(73) Assignee: Qure.ai Technologies Private Limited, Mumbai (IN)

(*) Notice: Subject to any disclaimer, the term of this patent is extended or adjusted under 35 U.S.C. 154(b) by 0 days.

(21) Appl. No.: 18/623,075

(22) Filed: Apr. 1, 2024

(65) Prior Publication Data
US 2024/0331872 A1    Oct. 3, 2024

(30) Foreign Application Priority Data
Mar. 31, 2023    (IN) .............................. 202321024806

(51) Int. Cl.
*G16H 50/30*    (2018.01)
*G06V 10/25*    (2022.01)
(Continued)

(52) U.S. Cl.
CPC ............. *G16H 50/30* (2018.01); *G06V 10/25* (2022.01); *G06V 10/26* (2022.01); *G06V 10/70* (2022.01); *G16H 30/20* (2018.01); *G16H 30/40* (2018.01); *G16H 50/20* (2018.01); *G06V 2201/031* (2022.01)

(58) Field of Classification Search
CPC ................................ G16H 50/30; G16F 50/20
See application file for complete search history.

(56) References Cited

U.S. PATENT DOCUMENTS

| 10,152,571 B1 | 12/2018 | Lyman et al. |
| 2005/0049497 A1* | 3/2005 | Krishnan ............... G16H 50/20 600/437 |

(Continued)

OTHER PUBLICATIONS

Qiwen Que; Ze Tang; Ruoshi Wang; Zeng Zeng; Jie Wang; Matthew Chua, Teo Sin Gee; Xulei Yang, Bharadwaj Veeravalli; CardioXNet: Automated Detection for Cardiomegaly Based on Deep Learning; 2018 40th Annual International Conference of the IEEE Engineering in Medicine and Biology Society (EMBC); IEEE; Jul. 18-21, 2018;10.1109/EMBC.2018.8512374.

(Continued)

*Primary Examiner* — Jay M. Patel

(57) ABSTRACT

A system and a method for detection of a heart failure risk is disclosed. The system may comprise a processor and a memory. The system (101) may receive one or more target chest X-ray image of a user. The system (101) may analyze one or more target chest X-ray image to identify and enhance one or more visual parameters of one or more RoI's. The system (101) may perform an anatomical segmentation on the one or more ROI's to detect one or more medical abnormalities from a set of medical abnormalities using the trained artificial intelligence model. The system (101) may calculate a confidence score of the heart failure risk in real time using a set of parameters corresponding to the detected one or more medical abnormalities from the set of medical abnormalities and further detect the heart failure risk for the user based on the confidence score.

14 Claims, 4 Drawing Sheets

(51) Int. Cl.
  *G06V 10/26*     (2022.01)
  *G06V 10/70*     (2022.01)
  *G16H 30/20*     (2018.01)
  *G16H 30/40*     (2018.01)
  *G16H 50/20*     (2018.01)

(56) References Cited

U.S. PATENT DOCUMENTS

| | | | | |
|---|---|---|---|---|
| 2007/0118399 | A1* | 5/2007 | Avinash | G16H 10/60 |
| | | | | 705/2 |
| 2011/0257545 | A1* | 10/2011 | Suri | A61B 8/5223 |
| | | | | 600/508 |
| 2015/0044098 | A1* | 2/2015 | Smart | A61B 5/0064 |
| | | | | 422/82.05 |
| 2015/0262372 | A1* | 9/2015 | Cardoso | G06F 18/22 |
| | | | | 382/131 |
| 2016/0253456 | A1* | 9/2016 | Goede | G06F 16/5866 |
| | | | | 705/3 |
| 2016/0267222 | A1* | 9/2016 | Larcom | G16H 30/20 |
| 2017/0351939 | A1* | 12/2017 | Madabhushi | G06T 7/11 |
| 2019/0156947 | A1* | 5/2019 | Nakamura | G16H 50/20 |
| 2019/0294984 | A1* | 9/2019 | Guttmann | G06V 40/10 |
| 2021/0241884 | A1* | 8/2021 | Swisher | G06V 10/82 |
| 2022/0007946 | A1* | 1/2022 | Ziegle | A61B 8/08 |
| 2022/0037018 | A1* | 2/2022 | Goede | G06F 18/251 |
| 2022/0076414 | A1 | 3/2022 | Park et al. | |
| 2022/0383986 | A1* | 12/2022 | Popescu | G16H 30/40 |
| 2023/0011031 | A1* | 1/2023 | Goede | G16H 30/40 |
| 2023/0230241 | A1* | 7/2023 | Lure | G16H 50/00 |
| | | | | 382/128 |

OTHER PUBLICATIONS

Takuya Matsumoto; Satoshi Kodera, MD; Hiroki Shinohara, MD; Hirotaka Ieki, MD; Toshihiro Yamaguchi, MD; Yasutomi Higashikuni, MD; Arihiro Kiyosue, MD; Kaoru Ito, MD; Jiro Ando, MD; Eiki Takimoto, MD; Hiroshi Akazawa, MD; Hiroyuki Morita, MD and Issei Komuro, MD; Diagnosing Heart Failure from Chest X-Ray Images Using Deep Learning; International Heart Journal; Int Heart J 2020; 61 Issue 4 781-786.

Sema Candemir; Sivaramakrishnan Rajaraman; George Thoma; Sameer Antani; Deep Learning for Grading Cardiomegaly Severity in Chest X-Rays: An Investigation; 2018 IEEE Life Sciences Conference (LSC); Oct. 28-30, 2018;10.1109/LSC.2018.8572113; IEEE.

\* cited by examiner

SYSTEM AND METHOD FOR DETECTION OF A HEART FAILURE RISK

CROSS-REFERENCE TO RELATED APPLICATIONS AND PRIORITY

The present application claims priority from Indian Provisional Patent Application having Application Number 202321024806 filed on 31 Mar. 2023, incorporated herein by a reference.

TECHNICAL FIELD

The present disclosure relates to a system and method for detection of a heart failure risk.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Generally, when a patient is unwell there is a requirement for a patient to consult a doctor and get diagnosed. The consultation may involve usage of medical imaging techniques. In general practice, medical imaging techniques have always been crucial for diagnosis and monitoring of medical conditions. Such diagnostic techniques are known to necessarily require highly skilled medical professionals such as radiologists, pulmonologists, cardiologists. Further, conventional instruments used for the diagnostic techniques require appropriate set up, assembling, and operational skills to be worked upon. The medical imaging techniques comprise an ultrasound imaging, doppler ultrasound measurements, Magnetic Resonance Imaging (MRI), X-rays, fluoroscopic imaging techniques and the like. Medical imaging techniques assist in diagnosis as well as treatment of medical conditions. It is well known that obtaining an X ray requires at least skilled medical professionals, a lab facility, or a diagnostic centre. Further, an interpretation of the X ray report requires skilled professionals such as radiologists and doctors as well.

Typically, non-clinicians such as nurses, physiotherapists, heath care providers and patients are not trained and equipped to perform the conventional diagnostic techniques. It may be understood that consulting a doctor, seeking an appointment for conventional X-ray, undergoing the X-ray procedure, procuring the X-ray reports, and then getting the X-ray reports interpreted by doctors, radiologists and the like may become a time-consuming process. Further, there is a possibility of partial diagnosis or an incomplete diagnosis if the X-ray image is not interpreted accurately and timely. Consequently, there may be a delay or negligence in detection of serious life-threatening medical conditions such as heart failure.

Therefore, there is a long-standing need for a system and a method for detecting a heart failure risk which can alleviate at least the drawbacks and/or challenges associated with the conventional system.

SUMMARY

The present disclosure overcomes one or more shortcomings of the prior art and provides additional advantages discussed throughout the present disclosure. Additional features and advantages are realized through the techniques of the present disclosure. Other embodiments and aspects of the disclosure are described in detail herein and are considered a part of the claimed disclosure.

The present disclosure has been made in order to solve the problems, and it is an object of the present disclosure to provide a system and method for detecting a heart failure risk.

In one implementation, a system for detecting heart failure risk is disclosed. The system may comprise a processor and a memory coupled with the processor. The processor may be configured for executing programmed instructions stored in the memory. The processor may execute instructions for training an artificial intelligence model using a training dataset, wherein the training dataset includes a plurality of chest X-ray image. The processor may execute instructions for receiving one or more target chest X-ray images of a user. The processor may execute instructions for analyzing the one or more target chest X-ray image for identifying one or more Region of Interest (RoI's). The processor may execute instructions for enhancing one or more visual parameters of one or more RoI's. The processor may execute instructions for performing an anatomical segmentation on the one or more ROI's to detect one or more medical abnormalities from a set of medical abnormalities using the trained artificial intelligence model. The processor may execute instructions for calculating a confidence score of the heart failure risk in real time using a set of parameters corresponding to the detected one or more medical abnormalities from the set of medical abnormalities. The processor may execute instructions detecting the heart failure risk for the user based on the confidence score.

In another implementation, a method for detecting heart failure risk is disclosed. The method may include training, via a processor, an artificial intelligence model using a training dataset, wherein the training dataset includes a set of chest X-ray image. The method may further include receiving, via the processor, one or more target chest X-ray images of a user. The method may further include analyzing, via the processor, the one or more target chest X-ray images for identifying one or more Region of Interests (RoI's). The method may further include enhancing, via the processor, one or more visual parameters of one or more RoI's. The method may further include performing, via the processor, an anatomical segmentation on the one or more ROI's to detect one or more medical abnormalities from a set of medical abnormalities using the trained artificial intelligence model. The method may further include calculating, via the processor, a confidence score of the heart failure risk in real time using a set of parameters corresponding to the detected one or more medical abnormalities from the set of medical abnormalities. The method may further detect, via the processor, the heart failure risk for the user based on the confidence score.

BRIEF DESCRIPTION OF DRAWINGS

The detailed description is described with reference to the accompanying Figures. In the Figures, the left-most digit(s) of a reference number identifies the Figure in which the reference number first appears. The same numbers are used throughout the drawings to refer like features and components.

DETAILED DESCRIPTION

Figure 1:
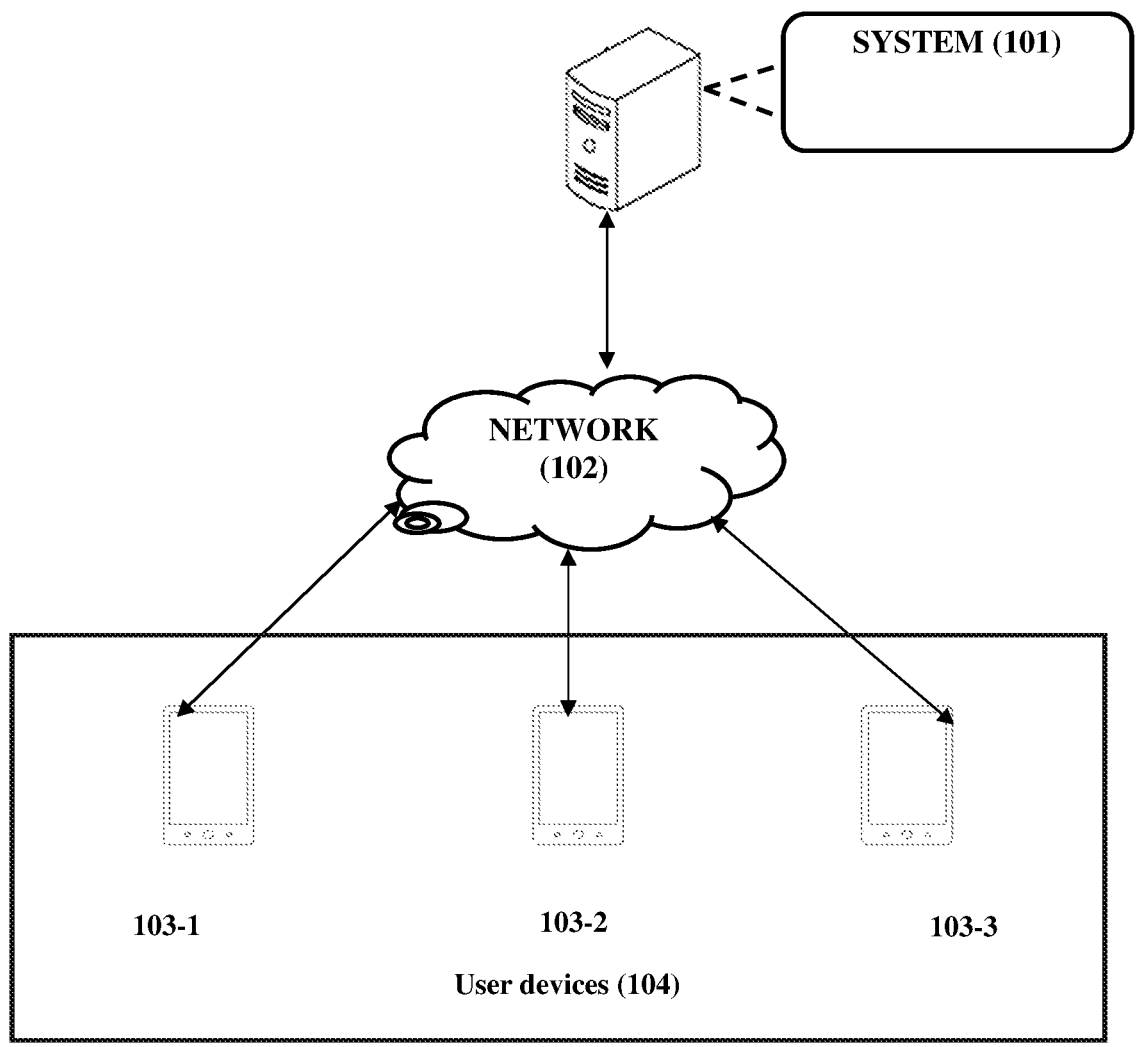
FIG. 1 illustrates a network implementation (100) of the system (101) for detecting a heart failure risk, in accordance with an embodiment of the present disclosure.

It should be understood that this invention is not limited to the particular methodology, protocols, and systems, etc., described herein and as such may vary. The terminology used herein is for the purpose of describing particular embodiments only and is not intended to limit the scope of the present invention, which is defined solely by the claims.

The terms "comprise", "comprising", "include(s)", or any other variations thereof, are intended to cover a non-exclusive inclusion, such that a setup, system or method that comprises a list of components or steps does not include only those components or steps but may include other components or steps not expressly listed or inherent to such setup or system or method. In other words, one or more elements in a system or apparatus preceded by "comprises" does not, without more constraints, preclude the existence of other elements or additional elements in the system or apparatus.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures, or characteristics may be combined in any suitable manner in one or more embodiments.

As used in the specification and appended claims, unless specified to the contrary, the following terms have the meaning indicated below.

"Natural language processing (NLP)" refers to a way for computers to analyze, understand, and derive meaning from human language in a smart and useful way. By utilizing NLP, developers can organize and structure knowledge to perform tasks such as automatic summarization, translation named entity recognition, relationship extraction, sentiment analysis, speech recognition, and topic segmentation.

The present disclosure illustrates the use of "Artificial intelligence (AI)" in medical image processing. AI is a theory, method, technology and application system that uses a digital computer, or a machine controlled by a digital computer to simulate, extend and expand human intelligence, perceive the environment, acquire knowledge, and use knowledge to obtain the best results. In other words, artificial intelligence is a comprehensive technology of computer science, which attempts to understand the essence of intelligence and produce a new kind of intelligent machine that can react in a similar way to human intelligence. Artificial intelligence is to study the design principles and implementation methods of various intelligent machines, so that the machines have the functions of perception, reasoning and decision-making. AI technology is a comprehensive discipline, covering a wide range of fields, including both hardware-level technology and software-level technology. Basic artificial intelligence technologies generally include technologies such as sensors, dedicated artificial intelligence chips, cloud computing, distributed storage, big data processing technologies, operation/interaction systems, and mechatronics. Artificial intelligence software technology mainly includes computer vision technology, speech processing technology, natural language processing technology, and machine learning/deep learning.

The present disclosure illustrates various techniques and configurations that enable the integration and use of machine learning analysis in a data-driven image evaluation workflow. For example, machine learning analysis (such as trained models of image detection of certain medical conditions) may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional). For example, machine learning analysis may receive and process images from medical imaging procedure data, to identify trained structures, conditions, and conditions within images of a particular study. The machine learning analysis may result in the automated detection, indication, or confirmation of certain medical conditions within the images, such as the detection of urgent or life-critical medical conditions, clinically serious abnormalities, and other key findings. Based on the result of the machine learning analysis, the medical evaluation for the images and the associated imaging procedure may be prioritized, or otherwise changed or modified. Further, the detection of the medical conditions may be used to assist the assignment of the medical imaging data to particular evaluators, the evaluation process for the medical imaging data, or implement other actions prior to, or concurrent with, the medical imaging evaluation (or the generation of a data item such as a report from such medical imaging evaluation).

As further discussed herein, the machine learning analysis may be provided on behalf of any number of machine learning algorithms and trained models, including but not limited to deep learning models (also known as deep machine learning, or hierarchical models) that have been trained to perform image recognition tasks, particularly for certain types of medical conditions upon medical images of human anatomy and anatomical representations. As used herein, the term "machine learning" is used to refer to the various classes of artificial intelligence algorithms and algorithm-driven approaches that are capable of performing machine driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described medical imaging evaluation may be supplemented or substituted by any number of other algorithm-based approaches, including variations of artificial neural networks, learning-capable algorithms, trainable object classifications, and other artificial intelligence processing techniques.

In some of the following examples, reference is made to radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a licensed and credentialed radiologist. It will be understood that the applicability of the presently described techniques and systems will extend to a wide variety of imaging data (and other data representations) produced by various medical procedures and specialties, including those not involving traditional radiology imaging modalities. Such specialties include, but are not limited, to pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the performance of the data recognition and workflow modification techniques described herein may apply to a variety of medical image data types, settings, and use cases, including captured static images and multi-image (e.g. video) representations.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure relates to a system (101) for detecting heart failure risk. Now referring to FIG. 1, a network implementation (100) of the system (101) for detecting the heart failure risk, is illustrated in accordance with an embodiment of the present disclosure.

Although the present subject matter explained considering that the system (101) is implemented on a server is, it may be understood that the system (101) may also be implemented in a variety of computing systems, such as a laptop computer, a desktop computer, a notebook, a workstation, a mainframe computer, a server, a network server, and the like. It will be understood that the system (101) may be accessed by multiple users through one or more user devices (103-1, 103-2 . . . 103-N, collectively referred to as user 103 hereinafter), or applications residing on the user devices (103). Examples of the user devices (103) may include, but are not limited to, a portable computer, a personal digital assistant, a handheld device, and a workstation. The user devices (103) are communicatively coupled to the system (101) through a network (102).

In one implementation, the network (102) may be a wireless network, a wired network or a combination thereof. The network (102) can be implemented as one of the different types of networks, such as intranet, local area network (LAN), wide area network (WAN), the internet, and the like. The network (102) may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network (102) may include a variety of network devices, including routers, bridges, servers, computing devices, storage devices, and the like.

The aforementioned devices may support communication over one or more types of networks in accordance with the described embodiments. For example, some computing devices and networks may support communications over a Wide Area Network (WAN), the Internet, a telephone network (e.g., analog, digital, POTS, PSTN, ISDN, xDSL), a mobile telephone network (e.g., CDMA, GSM, NDAC, TDMA, E-TDMA, NAMPS, WCDMA, CDMA-2000, UMTS, 3G, 4G), a radio network, a television network, a cable network, an optical network (e.g., PON), a satellite network (e.g., VSAT), a packet-switched network, a circuit-switched network, a public network, a private network, and/or other wired or wireless communications network configured to carry data. Computing devices and networks also may support wireless wide area network (WWAN) communications services including Internet access such as EV-DO, EV-DV, CDMA/1xRTT, GSM/GPRS, EDGE, HSDPA, HSUPA, and others.

Figure 2:
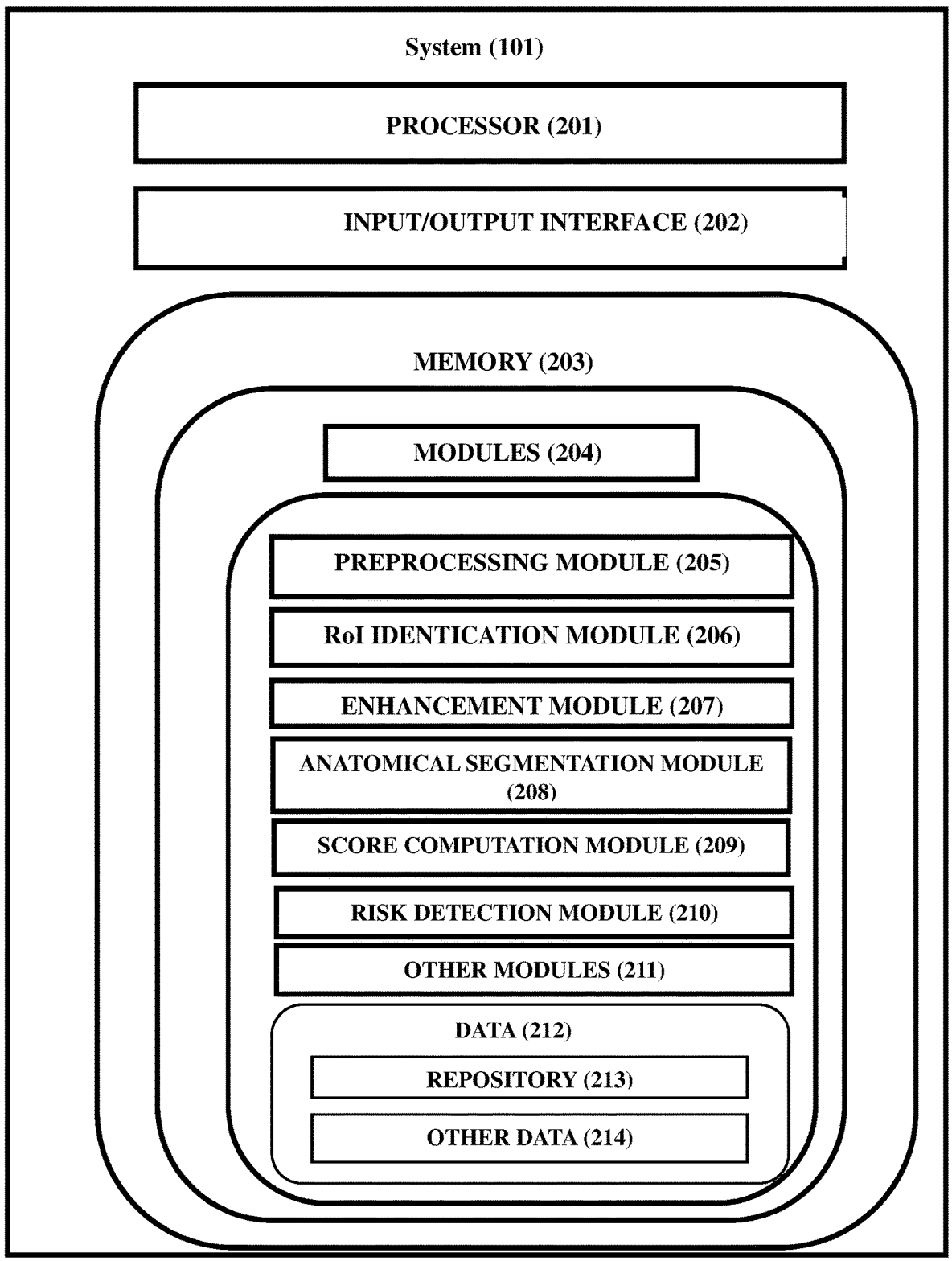
FIG. 2 illustrates, components of the system (101) for detecting a heart failure risk in accordance with the embodiment of the present disclosure.

The aforementioned devices and networks may support wireless local area network (WLAN) and/or wireless metropolitan area network (WMAN) data communications functionality in accordance with Institute of Electrical and Electronics Engineers (IEEE) standards, protocols, and variants such as IEEE 802.11 ("WiFi"), IEEE 802.16 ("WiMAX"), IEEE 802.20x ("Mobile-Fi"), and others. Computing devices and networks also may support short range communication such as a wireless personal area network (WPAN) communication, Bluetooth® data communication, infrared (IR) communication, near-field communication, electromagnetic induction (EMI) communication, passive or active RFID communication, micro-impulse radar (MIR), ultra-wide band (UWB) communication, automatic identification and data capture (AIDC) communication, and others Referring now to FIG. 2, components of the system (101) are illustrated in accordance with an embodiment of the present subject matter. In one embodiment, the system (101) may include at least one processor (201), an input/output (I/O) interface (202), and a memory (203). The at least one processor (201) may be implemented as one or more microprocessors, microcomputers, microcontrollers, digital signal processors, central processing units, state machines, logic circuitries, and/or any devices that manipulate signals based on operational instructions. Among other capabilities, at least one processor (201) is configured to fetch and execute computer-readable instructions stored in the memory (203).

The I/O interface (202) may include a variety of software and hardware interfaces, for example, a web interface, a graphical user interface, and the like. The I/O interface (202) may allow the system (101) to interact with a user directly or through the client devices (103). Further, the I/O interface 202 may enable the system 101 to communicate with other computing devices, such as web servers and external data servers (not shown). The I/O interface 202 can facilitate multiple communications within a wide variety of networks and protocol types, including wired networks, for example, LAN, cable, etc., and wireless networks, such as WLAN, cellular, or satellite. The I/O interface 202 may include one or more ports for connecting a number of devices to one another or to another server.

The memory 203 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. The memory (203) may include modules (204) and data (211).

The modules (204) include routines, programs, objects, components, data structures, etc., which perform particular tasks or implement particular abstract data types. In one implementation, the modules (204) may include a pre-processing module (205), an RoI identification module (206), an enhancement module (207), an anatomical segmentation module (208), a score computation module (209), a risk detection module (210) and other modules (211). The other modules (211) may include programs or coded instructions that supplement applications and functions of the system (101).

The data (212), amongst other things, serves as a repository for storing data processed, received, and generated by one or more of the modules (204). The data 212 may also include repository (213) and other data (214). The other data (214) may include data generated as a result of the execution of one or more modules in the other module (211).

In one implementation, at first, a user may use the user device (103) to access the system (101) via the I/O interface (202). The user may register themselves using the I/O interface (202) in order to access the system (101).

The system (101) may comprise an artificial intelligence model. The processor (201) may be configured for training the artificial intelligence model using a training dataset. The training dataset may include, but not limited to, a set of chest X-ray images. In one exemplary embodiment, a medical survey of 5000 patients may be carried out a public university in Turkey. Further, the patients in the survey may be scanned due to a medical condition resulting in chest pain, pneumonia, high blood pressure and the like. Further, the patients may be advised to undergo a medical imaging technique such as X-ray technique and the chest X-ray image be obtained for each of the patient i.e., around 5000 chest X-ray images may be acquired for the patients participating in the survey. The training dataset of the chest X-ray images may be used for training the artificial intelligence model. The system (101) may be pre-trained for detecting the heart failure risk in real time.

In one embodiment, the system (101) may comprise a development dataset. The development dataset may comprise the training dataset and an internal validation dataset. A small amount of the training dataset may be used to select the hyperparameters and rest of the training dataset may be used to train the algorithms. In one embodiment, the convolutional neural network may be used for training has U2-Net architectures, which consists of custom encoder and decoder like the popular U-Net architecture but with a two-level nesting underneath.

The nested design helps with capturing more contextual information from different scales due to the presence of receptive fields of different size and increases the depth of the architecture without adding too much additional computational cost. It is trained with a binary cross-entropy loss function for pixel level probability. Stochastic gradient descent with a batch size of 6 is used. Learning rate started at 0.05 with a one cycle scheduler and may be trained for 100 epochs.

During the training, all the scans in a batch are augmented randomly using the following methods such as resizing the image by a random factor between 1 and 1.15, randomly cropping the resized image to respective sizes required by CNN models, pixel intensity augmentation by varying brightness, contrast, and gamma value. The real-world X-ray images have a natural variation depending on the settings, voltage, manufacturer etc. The above augmentations are intended to make the models robust to this variance. Data augmentation is a well-accepted technique in the training of deep learning algorithms, with no risks associated, if augmented data is only used for training and not for validation or testing.

Further, network weights are initialized for all the layers in the network. In one embodiment, the models are trained on a device with AMD Ryzen 2920X processor, with 3RTX 2080 Ti GPUs (each of 12 GB memory) and 64 GM of RAM using pytorch framework. The training time may be six hours for each model.

In one embodiment, the development dataset may refer to the database of the chest X-rays that are used to develop and refine the training algorithm.

The distribution of the development data is summarized below table:

TABLE 1 distribution of development dataset

| | No. of scans |
|---|---|
| Country of Origin | |
| Medall | 1874 |
| FTS | 100 |
| Vikram Hospitals | 67 |
| Columbia Asia Hospital | 23 |
| Gender | |
| Male | 1640 |
| female | 1836 |
| NA | 524 |
| Age range | |
| <22 | 429 |
| ≥22 < 35 | 418 |
| >=35&<60 | 660 |
| >=60&<85 | 38 |
| NA | 1470 |
| X-ray Manufacturer | |
| FUJIFILM Corporation | 317 |
| Agfa | 67 |
| NA | 51 |
| Canon Inc. | 49 |
| CARESTREAM | 23 |
| Carestream Health | 19 |
| Samsung Electronics | 16 |
| Allengers DR | 13 |
| NA | 14 |
| Oehm und Rehbein GmbH | 10 |
| CARESTREAM HEALTH | 6 |
| KODAK | 5 |
| Philips Medical Systems | 3 |
| iCRco, Inc. | 2 |
| SIEMENS | 2 |
| KONICA MINOLTA | 1 |
| FUJI PHOTO FILM Co., ltd. | 1 |
| 3DISC | 1 |

The processor (201) may be configured for receiving one or more target chest X-ray image of a user via I/O interface (202). In another embodiment, the processor (201) may be configured for using Natural language processing (NLP) technique/algorithm to parse unstructured radiology reports and extract information about the presence of abnormalities in the one or more chest X-ray scans. These extracted findings are used as labels when training a deep learning algorithm. The extracted findings comprise locations, severity, size, shape and texture. The labels comprise scan-level labels, ROI level labels and pixel level labels.

The NLP algorithm was constructed using a thoracic imaging glossary, curated by a panel of radiologists and tailored to be consistent with the predefined set of medical abnormality definitions. This algorithm is rule-based as opposed to machine-learning based NLP. See John Zech, et. al., Natural Language-based Machine Learning Models for the Annotation of Clinical Radiology Reports, Radiology (2018). Rule-based systems performed better than learned methods, probably because of the vast amount of domain specific knowledge that had to be imparted which would require large amounts of annotated data. The proprietary NLP algorithm is essentially a large set of rules.

Since data was collected from multiple sources, the reporting standards were not consistent. The same finding can be noted in several different formats. For example, the finding Blunted Costophrenic angle can be reported in either of the following ways: "CP angle is obliterated"; "Hazy costophrenic angles"; or "Obscured CP angle". The system collected all the wordings that can be used to report findings and created a rule for each finding.

In addition to these rules that pick mentions of abnormal findings from reports, to obtain the final labels, the system performs negation detection, uncertainty detection and a set of standard NLP techniques to account for formatting and grammatical issues. The system also extracts qualifiers like left, right, upper zone, etc. that serve as additional labels for a given image. The final algorithm is validated by expert radiologists. A group of experts were given the abnormality definitions. The findings extracted by the NLP algorithm were compared against the findings extracted by the experts. Results from this validation are presented in the main text.

Table 2 lists definitions that were used when extracting radiological findings from the reports:

TABLE 2

Abnormality definitions

| Finding | Definition for tag extraction from radiology reports | Definition for radiologist review |
|---|---|---|
| Normal | 'No abnormality detected' or 'Normal' | Normal X-ray |
| Blunted CP angle | Blunted CP angle | CP Angle blunted or obscured. Could be due to pleural effusion or pleural thickening |
| Calcification | Calcification | All calcifications on X-ray including but not limited to aortic arch calcification, rib calcifications, calcified pulmonary densities and microcalcifications |
| Cardiomegaly | Cardiomegaly | Cardiothoracic ratio > 0.5 |
| Cavity | Pulmonary cavity | Pulmonary cavity |
| Consolidation | Consolidation, pneumonia or airbronchogram | Pulmonary consolidation |
| Fibrosis | Fibrosis | Any evidence of lung fibrosis, including interstitial fibrosis; fibrocavitary lesion |
| Hilar prominence | Hilar enlargement, prominent hilum or hilar lymphadenopathy | Enlarged or prominent hilum or including hilar lymphadenopathy |
| Opacity | Any lung field opacity or opacities, shadow or density including but not limited to infiltrate, consolidation, mass, nodule, pulmonary calcification, and fibrosis | Any lung field opacity or multiple opacities including but not limited to infiltrate; consolidation, mass, nodule, pulmonary, calcification, and fibrosis. Pleural abnormalities not included under this tag |
| Pleural Effusion | Pleural Effusion | Pleural Effusion |

These findings are referred as tags. Tag extraction accuracy was measured versus a set of reports where abnormalities were manually extracted.

The processor (201) may be configured to execute instructions stored in the pre-processing module (205) for pre-processing of the one or more target chest X-ray image. The pre-processing of the one or more target chest X-ray image may comprise geometric transformations of the chest X-ray image including rotating, resizing, scaling, translation and enhancement in features of the chest X-ray image to suppress unwanted distortions. In one embodiment, the one or more target chest X-rays images may be resized to a standard size and a set of standard normalizations may be applied to reduce source dependent variation. The resizing operation involves downsampling the original chest X-ray image. Though downsampling implies loss of potentially valuable information and may help models to train and detect better by overcoming the curse of dimensionality and warranted by the current state of AI. Additionally, the size of the image impacts the speed of inference significantly. Given the fact that X-Rays are not as standardized as other medical imaging modalities like CTs and MRIs, a large number of tag specific data augmentations aimed at making the models robust to variability in manufacturer/model used to acquire, exposure, noise are used while training.

In one exemplary embodiment, the one or more target chest X-ray images are in digital imaging and communication (DICOM) format. The pre-processing module may comprise a scan filtering and series picking submodule (not shown in the Figure). The scan filtering and series picking submodule may be configured to check DICOM tags on each series to determine if it meets inclusion or exclusion criteria. If the scan filtering and series picking submodule determines that the DICOM is not a chest X-ray, then it is not proceeded further. A response indicative of invalid DICOM is sent back to the user. If the criteria is not met, the scan may not be proceeded further. The DICOM tags may be at least one of a list including, but not limited to, study description, series description, Patient's age, modality, body parts examined, pixel spacing, photographic interpretation, screen minimum grayscale bit depth, pixel data, rows, columns, manufacturer etc. Further, the DICOM tags and description of DICOM tags are presented in the below table:

TABLE 3

DICOM tags

| DICOM tags used for series description | Tags description |
|---|---|
| Study description | Institution-generated description or classification of the Study (component) performed |
| Series Description | Description of the Series |
| Patient's Age | Age of the patient |
| Modality | Type of equipment that originally acquired the data used to create the images in this Series. |
| Body Part Examined | Text description of the part of the body examined. |
| Pixel Spacing | Physical distance in the patient between the center of each pixel, specified by a numeric pair-adjacent row spacing (delimiter) adjacent column spacing in mm |
| Photometric Interpretation | Specifies the intended interpretation of the pixel data |
| Screen Minimum Grayscale Bit Depth | Positive integer indicating the desired minimum number of grayscale bits per pixel of the screen. |
| Pixel Data | A data stream of the pixel samples that comprise the Image. |
| Rows | Number of rows in the image |
| Columns | Number of columns in the image |

TABLE 3-continued

DICOM tags

| DICOM tags used for series description | Tags description |
|---|---|
| Manufacturer | Manufacturer of the equipment that produced the Composite Instances. |

After the metadata check is complete, the pre-processing module may be configured to convert the DICOM into an image. In one exemplary embodiment, the image is in .png format. The image may be processed by each pre-trained convolution neural network, by performing a set of functions such as image reading, image normalization, image resizing.

In one embodiment, the pre-processing module may further comprise image reading submodule (not shown in the figure). The image reading submodule may be configured to receive metadata check data from the scan filtering and series picking submodule and to return a two-dimensional image to the pre-processing module.

The pre-processing module may be configured to perform normalization of the two-dimensional image. The pixel values in the two-dimensional image may belong to different statistical distributions with varied minimum and maximum values. The two-dimensional image (hereinafter referred as "image") may be normalized to values between 0 and 1 to reduce the variance in pixel values.

The pre-processing module (205) may be configured to resize the image to a standard size of 224×224 pixels for thorax and 960×960 pixels for heart using bilinear interpolation. Further, the resized image may be clipped to maintain pixel values between 0 and 1.

The processor (201) may be configured to execute instructions stored in the Region of Interests (RoI) identification module (206) for analyzing the one or more target chest X-ray images for identifying one or more Region of Interests (RoI's). In one embodiment, the one or more RoI's of the one or more target chest X-ray image may include a heart, lungs, blood vessels, and airways.

The RoI identification module (206) is completely rule-based and developed in close collaboration with radiologists. The output of the RoI identification module varies based on the medical abnormality. As an example, for pleural effusion, the RoI identification module (206) may identify two RoIs that cover the lower halves of the lung along with the costophrenic angles and a part of the diaphragm.

The processor (201) may be configured to execute instructions stored in the enhancement module (207) for enhancing one or more visual parameters of the one or more RoI's. In one embodiment, the one or more visual parameters may comprise a contrast level, brightness level, image sharpness, a clarity level and a box frame for the one or more RoI's of the one or more target chest X-ray image. The box frame may be a border or a boundary outlining the one or more RoI's. In one exemplary embodiment, if the one or more RoI's comprise a heart and lungs from the one or more target chest X-ray, then the box frame may be provided around the heart and lungs.

The processor (201) may be configured to execute instructions stored in the anatomical segmentation module (207) for performing an anatomical segmentation on the one or more RoI's to detect one or more medical abnormalities using the trained artificial intelligence model. In one embodiment, the anatomical segmentation may be carried out by one or more of an anatomical segmenter, an anatomical segmentation algorithm, a machine learning model, and a combination of the anatomical segmenter, the anatomical segmentation algorithm, and the machine learning model. In one embodiment, the set of medical abnormalities may include but not limited to cardiomegaly, pleural effusion, presence of Kerley B lines, and presence of pulmonary edema. In another embodiment, the set of medical abnormalities may be related to the lungs. Cardiomegaly may be understood as a medical condition characterized by an enlarged heart, wherein the heart exceeds beyond a normal range of size of heart in humans, as a ratio of the diameter of the chest. Pleural effusion may be understood as a medical condition characterized by a build-up of fluid between tissues that line the lungs and the chest. Kerley B line may be understood as an arrow like line or a horizontal line in the lung periphery that extends to the pleural surface. The presence of Kerley B lines denotes thickened, edematous interlobular septa often due to pulmonary edema. Pulmonary edema (or Pulmonary oedema) may be understood as a medical condition characterized by presence of excessive fluid in the lungs.

In one exemplary embodiment, the anatomical segmentation module (207) may be configured to perform a thorax or chest segmentation and a heart segmentation. The thorax segmentation may use U-Net architecture with Squeeze-and-Excitation ResNet (Se-Resnet) as encoder which provide the segmentations for left and right thorax.

The Se-ResNet is a deep learning architecture that combines two important innovations: the residual connections of ResNet and the squeeze-and-excitation (SE) blocks. The SE block is added after the convolutional layer in each residual block. The SE block consists of two operations:

1. Squeeze operation: This operation reduces the spatial dimensions of the feature maps by global average pooling, resulting in a channel descriptor vector.
2. Excitation operation: This operation models the interdependencies between the channels by passing the channel descriptor vector through two fully connected layers with ReLU activation functions. The output of the excitation operation is a set of channel weights that are applied to the original feature maps. The output of the SE block is then added to the original residual connection, and the process is repeated for the next residual block.

The UNet architecture consists of a contracting path and an expanding path, which forms a "U" shape. The contracting path is a series of convolutional layers followed by a pooling operation, which reduces the spatial dimensions of the feature maps. This path is designed to capture the context of the input image. The expanding path is a series of convolutional layers followed by an up sampling operation, which increases the spatial dimensions of the feature maps. This path is designed to localize the objects in the input image. Each layer in the expanding path concatenates the corresponding feature maps from the contracting path to capture the localization cues. The architecture also includes skip connections that connect corresponding layers in the contracting and expanding paths. The skip connections allow the network to reuse the low-level features from the contracting path, which improves the segmentation accuracy. The final layer of the UNet architecture is a pixel-wise classification layer that outputs a segmentation mask for each pixel in the input image. The output of the final layer is a binary mask that indicates whether a pixel belongs to the foreground or the background. The final architecture is replacement of encoder by SE-ResNet in the U-Net architecture The heart segmentation may use Unet++ model with Efficientnet-B7 architecture as an encoder. The architecture consists of a stem convolutional layer followed by a series of repeating blocks. Each repeating block consists of a series of convolutional layers, including depth wise separable convolutions, followed by a squeeze-and-excitation (SE) block and a skip connection. The depth wise separable convolutions used in EfficientNet-B7 are a type of convolutional layer that factorizes the standard convolution into two separate operations: a depth wise convolution that applies a single filter to each input channel, followed by a pointwise convolution that applies 1×1 filters to combine the channels. This approach reduces the computational cost of the convolutional layers while maintaining high accuracy.

The UNet++ architecture consists of two main paths: the encoder and decoder paths. The encoder path is like the UNet architecture and consists of a series of convolutional and pooling layers, which extract high-level features from the input image. The decoder path also consists of a series of convolutional layers, but it uses up sampling and concatenation operations to expand the feature maps. The key innovation of UNet++ is the addition of dense skip connections between the encoder and decoder paths. These connections allow the decoder path to access the high-level features extracted by the encoder path at different scales. The dense skip connections are constructed by concatenating the feature maps from the same level in the encoder and decoder paths. This allows the network to better capture the hierarchical information in the input image and improves the segmentation accuracy.

UNet++ also includes a nested structure to capture the multi-scale features of the input image. The nested structure consists of multiple branches, each with a different resolution, and the feature maps from each branch are concatenated and passed through a series of convolutional layers to generate the final segmentation mask.

The final architecture is replacement of encoder by SE-ResNet in the U-Net architecture.

In anatomical segmentation module (207), a training set of chest X-rays may be annotated at the pixel level with anatomical labels. A U-net based neural network was trained to output anatomical segmentation masks corresponding to the lungs, diaphragm, mediastinum and ribs. See Olaf Ronneberger, et. al., *U-net: Convolutional networks for biomedical image segmentation. Lecture Notes in Computer Science*, pages 234-241 (2015). These segmentation networks operate on 256×256 resized versions of the chest X-ray.

The system (101) may comprise a historical knowledge database for a set of patients diagnosed with the medical abnormalities such as cardiomegaly, pleural effusion, presence of Kerley B lines, and presence of pulmonary edema and suffering a risk of heart failure. In one example, the set of patients may consist of 1000 patients. In another example, the set of patients may consist of 10,000 patients.

The processor (201) may be configured to execute instructions stored in the score computation module (209) for calculating a confidence score of the heart failure risk in real time using a set of parameters corresponding to the detected one or more medical abnormalities from the set of medical abnormalities. In one embodiment, the set of parameters may comprise, but not be limited to, a ratio between a size of the heart and a size of a chest cavity, cardiac diameter, heart diameter, thorax diameter and a presence of fluid around a pair of lungs. The confidence score may indicate a level of heart failure risk in real time. The confidence score may also referred as "a heart failure risk score". The heart failure risk score may indicate a probability of risk of heart failure for the patient. The confidence score is a value between 0 and 1 which represents the likelihood of risk of heart failure, wherein 1 denotes maximum risk. In one embodiment, the confidence score may be calculated using a set of algorithms. In another embodiment, a machine learning model may be trained based on the set of algorithms to calculate the confidence score for the X-ray image.

In one embodiment, the heart failure score may be calculated by taking a weighted average of a probability score of each medical abnormality of the detected one or more medical abnormalities.

In one exemplary embodiment, the heart failure risk for a patient is determined based upon detection of medical abnormalities such as cardiomegaly and Pleural effusion. A neural network also called artificial neural network (ANN) or simulated neural networks (SNN), are a subset of machine learning and are the backbone of deep learning algorithms. The neural network may be configured calculate the probability score for each of the cardiomegaly and pleural effusion which ranges from 0 to 1. A higher score is indicative of a higher probability of the occurrence of the abnormality. Further, the neural network may be trained to calculate a heart failure risk score by taking a weighted average of the probability score of cardiomegaly and the probability score of pleural effusion. Further, the heart failure risk may be determined based the heart failure risk score.

The heart failure risk score may define the sensitivity & specificity of the model. The heart failure risk score may be adjusted to adapt to the health needs of the population or number of patients being screened.

In another exemplary embodiment, the heart failure risk for a patient is determined based upon detection of medical abnormalities such as cardiomegaly, Pleural effusion, Kerley B lines, cephalization of pulmonary vessels, artery-to-bronchus ratio. The neural network may be configured calculate the probability score for each of the cardiomegaly, pleural effusion, Kerley B lines, cephalization of pulmonary vessels, artery-to-bronchus ratio. A medical abnormality detection model may be developed for each medical abnormality. Further, weights may be assigned for each medical abnormality as shown in table 4:

TABLE 4 weights may be assigned for each medical abnormality

| Medical abnormality | Weight assigned |
|---|---|
| Cardiomegaly | 0.35 |
| Pleural effusion | 0.35 |
| Kerley B lines | 0.1 |
| Cephalization of pulmonary vessels | 0.1 |
| Artery-to-bronchus ratio | 0.1 |

Further, the neural network may be trained to calculate a heart failure risk score by taking a weighted average of the probability score of cardiomegaly, pleural effusion, Kerley B lines, Cephalization of pulmonary vessels and Artery-to-bronchus ratio.

The processor (201) may be configured to execute instructions stored in the risk detection module (210) for detecting the heart failure risk for the user based on the confidence score. The system (101) may provide a level the heart failure risk, wherein the level of the heart failure risk may include a high risk, a low risk, and a moderate risk for heart failure based on one or more confidence scores.

Figure 3:
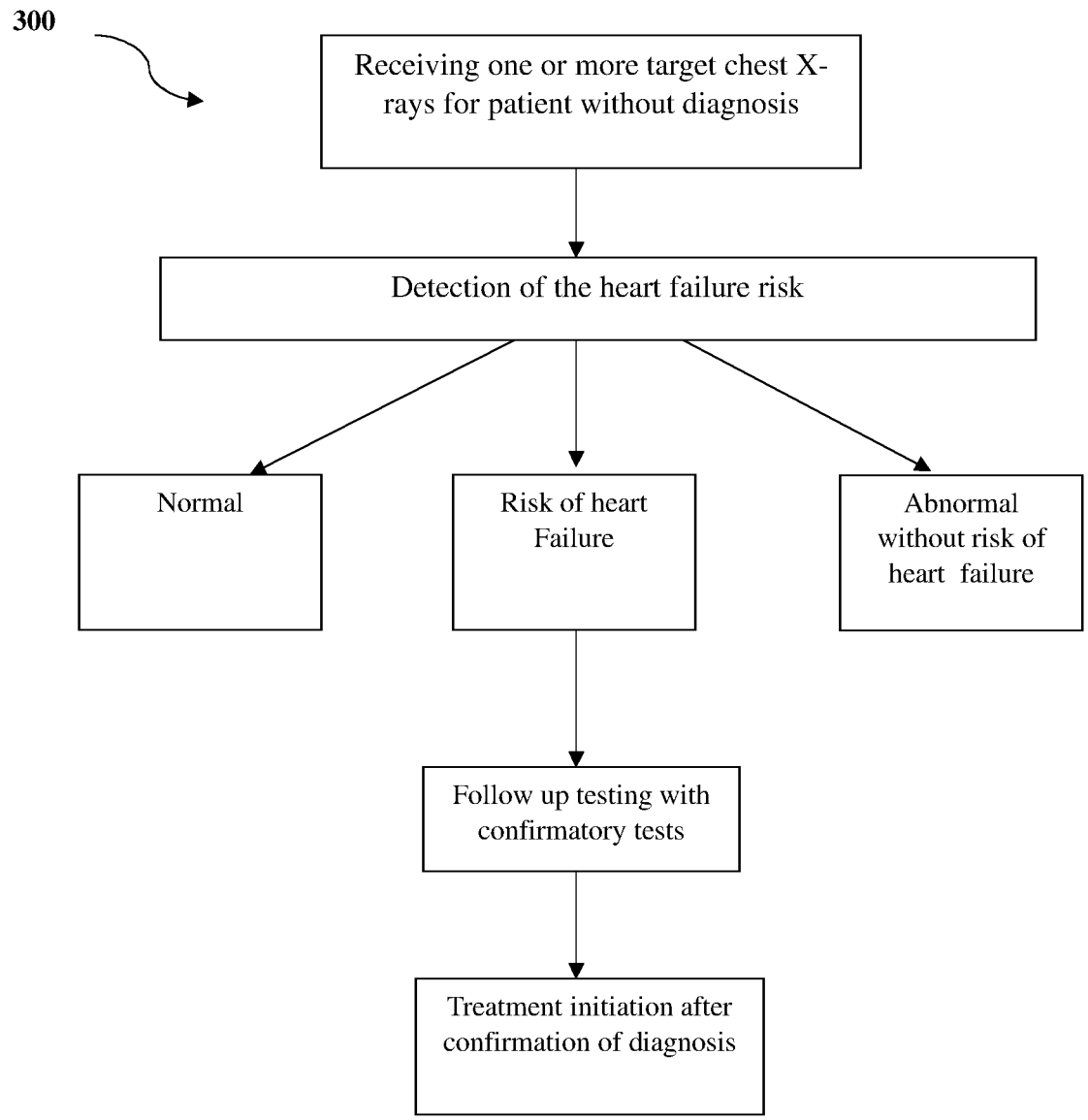
FIG. 3 illustrates, a flowchart (300) for detecting a heart failure risk for detecting the heart failure risk, in accordance with an exemplary embodiment of the present disclosure.

Now referring to FIG. 3, a flowchart (300) of the system (101) for detecting the heart failure risk, is illustrated in accordance with the exemplary embodiment of present disclosure. The system (101) may be configured for receiving the one or more target chest X-ray images for a patient without diagnosis of specific heart related problem. The system may detect the heart failure risk based on the confidence score. The system (101) may be configured for categorizing the patient in at least one category of normal category with no risk predicted for the heart failure, a risk of cardiac failure category for a user with the confidence score beyond a threshold value, and an abnormal category without risk of cardiac failure based on the confidence score.

In one exemplary embodiment, Youden's index is used for determining the threshold value based on the performance of internal validation test set.

The index is defined as:

$$J = \text{sensitivity} + \text{specificity} - 1$$

where sensitivity is the true positive rate (TPR) and specificity is the true negative rate (TNR).

The threshold which maximizes the Youden's index may be selected.

The internal test set results of the algorithm for pleural effusion is represented in table 5.

TABLE 5

| internal validation results | | | |
|---|---|---|---|
| Abnormality | Sensitivity | Specificity | AUC |
| Pleural Effusion | 0.9391 | 0.9232 | 0.962 (0.956-0.969) |

Further, the artificial intelligence model may be configured to determine prediction errors or residuals. Residuals are a measure of how far from regression line data points. The Root Mean Square Error (RMSE) is a measure of how far prediction spread out from measured ground true values. RMSE can be measured using following formula:

$$RMSE = \sqrt{(f - o)^2}$$

Whereas, f=expected value/outcome of chest X-ray; o=ground truth

In one embodiment, the prediction error using ground truth may be used to improve the accuracy of the artificial intelligence model.

In one exemplary embodiment, the artificial intelligence model reports the target abnormality and there is no target abnormality reported by ground truthers, referred as "False Positive (FP)". The artificial intelligence model does not report a target abnormality, and a target abnormality is reported by ground truthers, referred as "False Negative (FN)". The artificial intelligence model reports a target abnormality and a ground truther reports the same abnormality by the ground truth boundary, referred as "True Positive (TP)". The artificial intelligence model does not report any abnormality, and there is no target abnormality reported by ground truthers, referred as "True Negative (TN)".

The metrics are defined by the artificial intelligence model are as follows:

Sensitivity: The conditional probability of qXR-PTX-PE target abnormality—Yes flag given that abnormality is reported.

$$\text{Sensitivity} = TP/(TP + FN)$$

Specificity: The conditional probability of qXR-PTX-PE target abnormality—No flag given that abnormality is not reported.

$$\text{Sensitivity} = TN/(TN + FP)$$

AUC is measure of discrimination between cases with and without the target abnormality and this will be computed using a non-parametric method (Empirical AUC).

Further, the system (101) may be configured for recommending one or more follow-up confirmatory test the user based on the detection of the heart failure risk. In one example, the confirmatory test may comprise a NT Pro-B-type Natriuretic Peptide (NT-Pro BNP) test. In other example, the confirmatory test may comprise an 2D echocardiography test. Further, a treatment may be initiated for the patients with confirmed diagnosis of heart failure on the basis of the one or more confirmatory test, thereby preventing the worsening of heart failure risk in the patients.

Figure 4:
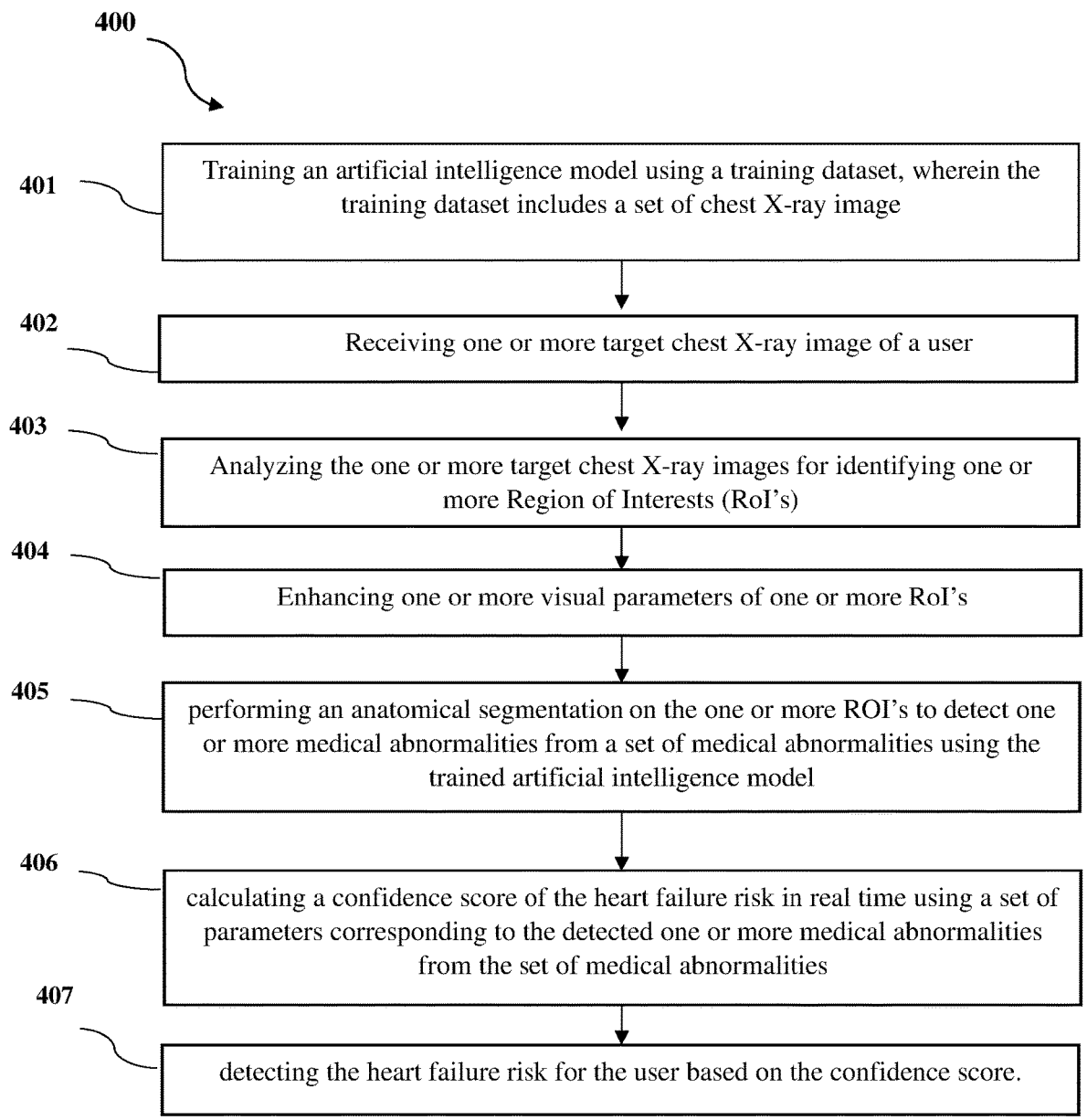
FIG. 4 illustrates, a stepwise method flowchart (400) for detecting the heart failure risk, in accordance with the embodiment of the present disclosure.

Now referring to FIG. 4, a stepwise method (400) for detecting the heart failure risk, is illustrated in accordance with the embodiment of present disclosure.

At step 401, the processor (201) may be configured for training an artificial intelligence model using a training dataset, wherein the training dataset includes a set of chest X-ray image.

At step 402, the processor (201) may be configured for receiving the one or more target chest X-ray image of the user.

At step 403, the processor (201) may be configured for analyzing the one or more target chest X-ray images for identifying the one or more Region of Interests (RoI's).

At step 404, the processor (201) may be configured for enhancing one or more visual parameters of one or more RoI's.

At step 405, the processor (201) may be configured for performing the anatomical segmentation on the one or more ROI's to detect one or more medical abnormalities from a set of medical abnormalities using the trained artificial intelligence model.

At step 406, the processor (201) may be configured for calculating a confidence score of the heart failure risk in real time using the set of parameters corresponding to the detected one or more medical abnormalities from the set of medical abnormalities.

At step 407, the processor (201) may be configured for detecting the heart failure risk for the user based on the confidence score.

Exemplary embodiments discussed above may provide certain advantages. Though not required to practice aspects of the disclosure, these advantages may include those provided by the following features.

Some embodiments of the system and the method may provide an artificially intelligent approach to analyze a chest X-ray image for users, medical professionals other than doctors, radiologists, etc.

Some embodiments of the system and the method may provide the heart failure risk score which identify suspected and previously undiagnosed heart failure patients and help them get timely treatment.

Some embodiments of the system and the method may provide early heart failure (HF) recognition which can reduce morbidity.

Some embodiments of the system and the method may reduce human skill and human time involved in analyzing and interpreting the chest X-ray images.

Some embodiments of the system and the method facilitate early detection of cardiomegaly, pleural effusion, presence of Kerley B lines, cephalization of pulmonary vessels, artery-to-bronchus ratio and presence of pulmonary edema.

Some embodiments of the system and the method provide risk assessment, confidence score, and detect a heart failure risk by analyzing the chest X-ray image.

We claim:

1. A system for detecting a heart failure risk, wherein the system comprising:
   a processor; and
   a memory coupled with the processor, wherein the processor is configured for executing programmed instructions stored in the memory for:
      training an artificial intelligence model using a training dataset, wherein the training dataset includes a set of chest X-ray images;
      receiving one or more target chest X-ray images of a user;
      analyzing the one or more target chest X-ray images for identifying one or more Region of Interests (RoI's);
      enhancing one or more visual parameters of the one or more RoI's;
      performing an anatomical segmentation on the one or more ROI's to detect one or more medical abnormalities from a set of medical abnormalities using the trained artificial intelligence model, wherein the anatomical segmentation is performed using Unet++ model with Efficientnet-B7 architecture as an encoder;
      calculating a confidence score of the heart failure risk in real time using a set of parameters corresponding to the detected one or more medical abnormalities from the set of medical abnormalities,
         wherein the set of parameters comprises thorax diameter, cardiac diameter, a presence of fluid around a pair of lungs, and a ratio between a size of the heart and a size of a chest cavity,
         wherein the confidence score is calculated by taking a weighted average of a probability score for each medical abnormality of the detected one or more medical abnormalities;
      detecting the heart failure risk for the user based on the confidence score, wherein the user is categorized in at least one category of normal category with no risk predicted for the heart failure, a risk of cardiac failure category for a user with the confidence score beyond a threshold value, and an abnormal category without risk of cardiac failure based on the confidence score; and
      recommending a follow-up confirmatory test to the user based on the detection of the heart failure risk.

2. The system as claimed in claim 1, further comprises pre-processing of the one or more target chest X-ray images, wherein the pre-processing comprises digital imaging and communication (DICOM) metadata filtering, image normalization, geometric transformations of the one or more target chest X-ray image including rotating, resizing, scaling, translation and enhancement in features of the one or more target chest X-ray image to suppress unwanted distortions.

3. The system as claimed in claim 1, wherein the set of medical abnormalities comprises cardiomegaly, pleural effusion, presence of Kerley B lines, cephalization of pulmonary vessels, artery-to-bronchus ratio, and presence of pulmonary edema.

4. The system as claimed in claim 1, wherein the one or more visual parameters comprise a contrast level, brightness level, image sharpness, a clarity level and a box frame for the one or more RoI's of the one or more target chest X-ray image, wherein the box frame is a border or a boundary outlining the one or more RoI's.

5. The system as claimed in claim 1, the anatomical segmentation is carried out by one or more of an anatomical segmenter, an anatomical segmentation algorithm, a machine learning model, and a combination of the anatomical segmenter, the anatomical segmentation algorithm, and the machine learning model.

6. The system as claimed in claim 1, wherein Natural Processing Language (NLP) technique is used for selecting one or more target chest X-ray image for the user and a corresponding radiology report.

7. The system as claimed in claim 6, wherein NLP technique is used to extract the set of medical abnormalities to generate extracted findings, wherein extracted findings are used as labels or tags for training a deep learning algorithm to detect the set of medical abnormalities.

8. A method for detecting a heart failure risk, wherein the method comprising:
   training, via a processor, an artificial intelligence model using a training dataset, wherein the training dataset includes a set of chest X-ray images;
   receiving, via the processor, one or more target chest X-ray images of a user;
   analyzing, via the processor, the one or more target chest X-ray images for identifying one or more Region of Interest (RoI's);
   enhancing, via the processor, one or more visual parameters of one or more RoI's;
   performing, via the processor, an anatomical segmentation on the one or more ROI's to detect one or more medical abnormalities from a set of medical abnormalities using the trained artificial intelligence model, wherein the anatomical segmentation is performed using Unet++ model with Efficientnet-B7 architecture as an encoder;
   calculating, via the processor, a confidence score of the heart failure risk in real time using a set of parameters corresponding to the detected one or more medical abnormalities from the set of medical abnormalities,
      wherein the set of parameters comprises thorax diameter, cardiac diameter, a presence of fluid around a pair of lungs, and a ratio between a size of the heart and a size of a chest cavity,
      wherein the confidence score is calculated by taking a weighted average of a probability score for each medical abnormality of the detected one or more medical abnormalities;
   detecting, via the processor, the heart failure risk for the user based on the confidence score, wherein the user is categorized in at least one category of normal category with no risk predicted for the heart failure, a risk of cardiac failure category for a user with the confidence score beyond a threshold value, and an abnormal category without risk of cardiac failure based on the confidence score; and recommending, via the processor, a follow-up confirmatory test to the user based on the detection of the heart failure risk.

9. The method as claimed in claim 8, further comprises pre-processing of the one or more target chest X-ray images, wherein the pre-processing comprises digital imaging and communication (DICOM) metadata filtering, image normalization, geometric transformations of the one or more target chest X-ray image including rotating, resizing, scaling, translation and enhancement in features of the one or more target chest X-ray image to suppress unwanted distortions.

10. The method as claimed in claim 8, wherein the set of medical abnormalities comprises cardiomegaly, pleural effusion, presence of Kerley B lines, cephalization of pulmonary vessels, artery-to-bronchus ratio, and presence of pulmonary edema.

11. The method as claimed in claim 8, wherein the one or more visual parameters comprise a contrast level, brightness level, image sharpness, a clarity level and a box frame for the one or more RoI's of the one or more target chest X-ray image, wherein the box frame is a border or a boundary outlining the one or more RoI.

12. The method as claimed in claim 8, the anatomical segmentation is carried out by one or more of an anatomical segmenter, an anatomical segmentation algorithm, a machine learning model, and a combination of the anatomical segmenter, the anatomical segmentation algorithm, and the machine learning model.

13. The method as claimed in claim 8, wherein Natural Processing Language (NLP) technique is used for selecting one or more target chest X-ray image for the user and a corresponding radiology report.

14. The method as claimed in claim 13, wherein NLP technique is used to extract the set of medical abnormalities to generate extracted findings, wherein extracted findings are used as labels or tags for training a deep learning algorithm to detect the set of medical abnormalities.

* * * * *